US005534775A

United States Patent [19]
Lam et al.

[11] Patent Number: 5,534,775
[45] Date of Patent: Jul. 9, 1996

[54] METHOD AND APPARATUS FOR NONCONTACT MAGNETIC PARTICLE STRAY MAGNETIC FLUX TESTING OF CYLINDRICAL MEMBERS

[75] Inventors: Clive C. Lam, Tomball; William W. Curtis, Jr.; Roy C. Grubbs, both of Houston, all of Tex.

[73] Assignee: ICO, Inc., Houston, Tex.

[21] Appl. No.: 33,091

[22] Filed: Mar. 16, 1993

[51] Int. Cl.$^6$ .................. G01N 27/84; G01N 27/72; G01R 33/12
[52] U.S. Cl. .................. 324/216; 324/226; 324/232
[58] Field of Search .................. 324/214, 215, 324/216, 226, 232, 227

[56] References Cited

U.S. PATENT DOCUMENTS

| | | | |
|---|---|---|---|
| 1,960,898 | 5/1934 | DeForest | 324/216 |
| 4,694,247 | 9/1987 | Meili et al. | 324/216 |
| 4,931,731 | 6/1990 | Jenks | 324/216 |

FOREIGN PATENT DOCUMENTS 0146157  9/1982  Japan ..................... 324/216

OTHER PUBLICATIONS

Plenum Publishing Corp. 1980 pp. 641–646, G. N. Dubinin et al. "Evaluation Of The Quality Of Pipes For The Petroleum Industry By The Results Of Nondestructive Inspection".
MAGNAFLUX CORPORATION, First Edition, Feb. 1967, Carl E. Betz "Principles Of Magnetic Particle Testing" pp. 189–190.
PROCEEDINGS OF THE CONFERENCE ON THE MECHANICS OF NONDESTRUCTIVE TESTING "Mechanics of Non–Destructive Testing" Sep. 1980, W. W. Stinchcomb.
INSPECTION AND TESTING, Mar. 1990 "ACFN–a new NDT technique" Martin Lugg.
IEEE TRANSACTIONS ON MAGNETICS, vol. 24, No. 6, Nov. 1988 "Computation of Three–Dimensional Electromagnetic Field In The Eddy–Current Testing Of Steel Pipes".
Plenum Publishing Corp. 1987 pp. 160–165, A. G. Aleksandrov "Indication Of Defects In Magnetic Particle Inspection Of Parts With The Use Of ADC Electromagnet".
Plenum Publishing Corp. 1979 pp.842–844, L. A. Khvatov et al. "An Automatic Checking system For Ferroprobe Tube Testers".
Plenum Publishing Corp. 1979 pp. 835–841, Yu, M. Bron et al. "ZOND" Automated Installation For Magnetic Inspection of the External Surface Of Circular Hot–Rolled Stock.

Primary Examiner—Walter E. Snow
Attorney, Agent, or Firm—Felsman, Bradley, Gunter & Dillon; Melvin A. Hunn

[57] ABSTRACT

A plurality of magnetic field members are provided, each for selectively generating a time-varying magnetic field for combination into a o time-varying composite longitudinal magnetic field with magnetic flux lines which are substantially aligned with the central longitudinal axis of the cylindrical ferromagnetic member. Additionally, a traverse magnetic field member is provided which selectively generates a time-varying traverse magnetic field with magnetic flux lines which are substantially traversed to the central longitudinal axis of the cylindrical ferromagnetic member. The plurality of magnetic field members and the traverse magnetic field member are maintained out of contact with the cylindrical ferromagnetic member. Magnetic particles are placed on selected portions of the cylindrical ferromagnetic member. A time-varying composite longitudinal magnetic field and a time-varying traverse magnetic field are applied to the cylindrical magnetic member, while it is being rotated. An operator inspects the outer and/or inner peripheral surfaces of the cylindrical member to detect defects therein from accumulations in magnetic particles at leakage fields corresponding to magnetic discontinuities of defects in the cylindrical ferromagnetic member.

16 Claims, 11 Drawing Sheets

METHOD AND APPARATUS FOR NONCONTACT MAGNETIC PARTICLE STRAY MAGNETIC FLUX TESTING OF CYLINDRICAL MEMBERS

BACKGROUND OF THE INVENTION

1. Field of the Invention

The present invention relates in general to techniques for non-invasively inspecting ferromagnetic parts, such as cylindrical or tubular members, and in particular relates to techniques for inspecting ferromagnetic cylindrical and tubular components through utilization of magnetic particles to identify stray flux which corresponds to defects in the ferromagnetic component.

2. Description of the Prior Art

Magnetic particle inspection techniques are one type of non-invasive inspection technique which may be utilized to locate surface and some sub-surface defects in ferromagnetic components. In magnetic particle inspection techniques, the ferromagnetic component is exposed to a magnetic field, which causes magnetic field flux lines to extend through the ferromagnetic component. Defects or aberrations in the ferromagnetic component will generate strong leakage fields, particularly if the defect is approximately perpendicular to the lines of the magnetic field flux. Dry or wet ferromagnetic particles are applied to the ferromagnetic component, are attracted by the leakage field, and collect at the site of the defect. This accumulation of magnetic particles indicates the location, size, and shape of the defect or aberration in the ferromagnetic component.

A broad overview of magnetic particle inspection techniques may be found in the following technical references, which are incorporated by reference herein as if fully set forth:

(1) "Nondestructive Testing Handbook", Second Edition, edited by T. J. Schmidt, K. Skeie, and P. McIntire, published by the American Society for Nondestructive Testing, Volume 6, Part 9, pages 405–420, entitled "Oil Field Applications of Magnetic Particle Testing";

(2) "NDE Handbook" (ISBN 0-408-04392-X) edited by Knud G. Bering, Chapter 17, entitled "Magnetic Particle Examination", published in an English-language edition by Butterworths in 1989.

(3) "Nondestructive Testing", authored by Warren J. McGonnagle, Chapter 10, entitled "Magnetic Methods", published by McGraw-Hill Book Company in 1961.

(4) "A Survey of Electromagnetic Methods of Nondestructive Testing", authored by W. Lord, and published by Plenum Press in 1980 in a book entitled "Mechanics of Nondestructive Testing" (ISBN 0-306-40567-9), edited by W. W. Stinchcomb, J. C. Duke, Jr., E. G. Hennecke II, and K. L. Reifsnider.

Two particular techniques merit detailed consideration. One technique is found in U.S. Pat. No. 4,931,731 which issued to Jenks on Jul. 5, 1991, and which is entitled "Magnetic Particle Inspection Apparatus With Enhanced Uniformity of Magnetization". The other technique is found in U.S. Pat. No. 4,694,247, which issued to Meili et al. on Sep. 15, 1987, and which is entitled "Method and Apparatus Including a Cushion of Pulverulent Magnetic Material for Stray Field Magnetic Testing of Ferromagnetic Parts".

In the technique of U.S. Pat. No. 4,931,731, two magnetic fields are generated: a magnetic field which passes longitudinally over the exterior surface of a tubular member, and a magnetic field which is concentrically disposed about the tubular member along its entire length. The longitudinal magnetic field is generated by passing a current through windings which are wound about a cylindrical core. The concentric magnetic field is generated by utilizing a current source to pass current directly through the tubular member. End pieces are coupled to each end of the tubular member to connect the tubular member within an electrical circuit with the current source. The current source produces a pulse train of current, which passes through the material of the tubular member and causes the concentric magnetic field to be generated about the tubular member.

There are several serious disadvantages with this approach, including:

(1) the end caps impede the operator's view of the full exterior surface of the tubular member while the field is active;

(2) the end caps also obstruct the operator's view of the interior surface of the tubular member while the current is being applied to the tubular member;

(3) with this approach, the tubular member cannot be rotated while the field is active, making it difficult for the inspector to quickly inspect all exterior surfaces of the tubular member;

(4) passing current directly through the tubular member can cause damage to the tubular member through undesirable electrical current arcs;

(5) it is difficult to pass a great number of tubular members through a workstation in assembly line fashion, since the end caps must be coupled to each tubular member; and (6) in this approach, for safety reasons, the operator cannot inspect the tubular member while the magnetic fields are active, since the electrical current passing through the tubular member can be dangerous to the operator.

The inspection technique of U.S. Pat. No. 4,694,247 is in general directed to a method and apparatus for detecting defects in the outer surface of ferromagnetic parts through utilization of pulverulent magnetic material and stray magnetic fields induced in the ferromagnetic part through application of a longitudinal magnetic field and a traverse magnetic field. In this technique, U-shaped electromagnets are utilized to generate a traverse magnetization of the part and in particular a lower portion of the part. A second U-shaped magnet is utilized to generate a longitudinal magnetic field which particularly affects a lower portion of the part. A bed of dry magnetic particles are provided in a bin which engages the lowermost portion of the ferromagnetic tubular member. The ferromagnetic tubular member is advanced through the bin of dry magnetic particles in a helical path to ensure that the entire outer periphery of the tubular member passes close to the bin of dry magnetic particles. The magnetic particles are attracted to the tubular member and are subject to detection as the part advances helically through stray magnetic fields which are generated by defects in the outer periphery of the tubular member.

There are several serious disadvantages with this approach, including:

(1) the operator's view of the most intense interaction between the induced stray magnetic field and the magnetic particles is obscured, since the most intense magnetic field is provided in only the lowermost portion of the tubular member while it is adjacent the bin of magnetic particles; therefore, detection of defects is entirely reliant upon the attraction of magnetic particles to the ferromagnetic tubular member and maintenance of the magnetic particles in that position while the tubular member rotates to allow a view of the region which was previously obscured;

(2) accordingly, the operator will never see the most direct and intense interaction between the stray magnetic field and the magnetic particles, introducing a substantial opportunity for failure in detection of all defects on the outer periphery of the tubular member;

(3) the fact that the tubular member must be passed adjacent the bin of magnetic particles slows the inspection process;

(4) the utilization of dry magnetic particles necessitates that cleaning operations be performed to remove the particles to prevent the particles from interfering with the operation of the tubular, and in particular to prevent the interference of the magnetic particles with make up of gas-tight threaded engagements with other tubular members;

(5) this technique does not allow for the inspection of any interior surface of the tubular member, such as the periphery of any central bore which extends through the tubular member; and (6) this technique requires the utilization of rather large U-shaped electromagnets, which are expensive.

SUMMARY OF THE INVENTION

It is one objective of the present invention to provide a method and apparatus for inspecting ferromagnetic cylindrical and tubular components wherein: (1) a time-varying longitudinal magnetic field is generated which is a combination of magnetic fields from a plurality of magnetic field members, and (2) a time-varying traverse magnetic field is generated with magnetic flux lines which are substantially traverse to the longitudinal magnetic field, and both fields are applied to the component.

It is another objective of the present invention to provide a method and apparatus for inspecting cylindrical and tubular ferromagnetic members for defects which provides an unobstructed view of (1) an outer peripheral portion of the cylindrical or tubular ferromagnetic member, and (2) an inner peripheral end portion of any central bore extending through the cylindrical or tubular ferromagnetic member.

It is yet another objective of the present invention to provide a method and apparatus for inspecting cylindrical and tubular ferromagnetic members for defects which includes as a component a controller for executing a program resident memory which is utilized to automatically perform at least one of the following steps: (1) placing magnetic particles on selected portions of the cylindrical or tubular ferromagnetic member; (2) applying a time-varying longitudinal magnetic field and a time-varying traverse magnetic field to the cylindrical or tubular ferromagnetic member; and (3) rotating the cylindrical or tubular ferromagnetic member.

It is yet another objective of the present invention to provide a method and apparatus for inspecting cylindrical and tubular ferromagnetic members for defects, wherein a time-varying longitudinal magnetic field is generated from a plurality of current carrying windings, each concentric the central longitudinal axis of the cylindrical or tubular magnetic member, and spaced apart along the central longitudinal axis of the cylindrical or tubular ferromagnetic member, wherein time-varying current is passed through the plurality of current-carrying windings in directions which ensure cancellation of magnetic field components adjacent the cylindrical or tubular ferromagnetic member which do not contribute to the longitudinal magnetic field.

It is still another objective of the present invention to provide a method and apparatus for inspecting a cylindrical or tubular ferromagnetic member for defects which allows inspection of the outer peripheral and/or inner peripheral surfaces of the end portions of ferromagnetic member while time-varying longitudinal and traverse magnetic fields are interacting with magnetic particles disposed on said outer and/or inner peripheral surfaces.

It is yet another objective of the present invention to provide a method and apparatus for inspecting cylindrical or tubular ferromagnetic members for defects, wherein a time-varying longitudinal magnetic field and a time-varying traverse magnetic field are successively applied to the cylindrical or tubular ferromagnetic member in a manner which ensures application of the magnetic field to all of the end portions of the ferromagnetic member, thus allowing the ferromagnetic member to be rotated during visual inspection for defects.

These and other objectives are achieved as is now described. When characterized broadly as a method, the present invention includes a number of method steps. In the preferred embodiment, a plurality of magnetic field members are provided, each for selectively generating a time-varying magnetic field for combination into a time-varying composite longitudinal magnetic field with magnetic flux lines which are substantially aligned with the central longitudinal axis of the cylindrical ferromagnetic member. Additionally, a traverse magnetic field member is provided which selectively generates a time-varying traverse magnetic field with magnetic flux lines which are substantially traversed to the central longitudinal axis of the cylindrical ferromagnetic member. The plurality of magnetic field members and the traverse magnetic field member are maintained out of contact with the cylindrical ferromagnetic member. Magnetic particles are placed on selected portions of the cylindrical ferromagnetic member. A time-varying composite longitudinal magnetic field and a time-varying traverse magnetic field are applied to the cylindrical magnetic member, while it is being rotated. An operator inspects the outer and/or inner peripheral surfaces of the cylindrical member to detect defects therein from accumulations in magnetic particles at leakage fields corresponding to magnetic discontinuities of defects in the cylindrical ferromagnetic member.

In the preferred embodiment, the plurality of magnetic field members comprise a plurality of current-carrying windings, each generally concentric to the central longitudinal axis of the cylindrical ferromagnetic member, and spaced apart along the central longitudinal axis. Preferably, the traverse magnetic field member comprises a ferromagnetic magnetic flux pathway with an air gap defined therein for axial passage of the cylindrical ferromagnetic member. In the particular embodiment described herein, time-varying current is passed through the plurality of current-carrying windings, in directions which ensure cancellation of magnetic field components adjacent the cylindrical ferromagnetic member which do not contribute to the time-varying composite longitudinal magnetic field.

Also, in the preferred embodiment of the present invention, the plurality of magnetic field members and the traverse magnetic field member are arranged to provide an unobstructed view of an outer peripheral portion of the cylindrical ferromagnetic member, and an inner peripheral portion of the end of any central bore extending through the cylindrical ferromagnetic member. This arrangement allows an operator to inspect both ends of a tubular member, including the outer peripheral area and the inner peripheral area. This technique is thus particularly useful for detecting defects in a tubular member in the region which is to be threaded.

In the preferred embodiment of the present invention, a controller is provided for executing a program resident in memory. The program is utilized to automatically perform at least one of the following steps: (1) advancing and retracting cylindrical or tubular ferromagnetic members through an inspection station (2) placing magnetic particles on selected portions of the cylindrical or tubular ferromagnetic member, including outer peripheral portions and inner peripheral portions; (3) applying a time-varying longitudinal magnetic field and a time-varying traverse magnetic field to the cylindrical or tubular ferromagnetic member; and (4) rotating the cylindrical or tubular ferromagnetic member.

Additional objectives, features and advantages will be apparent in the written description which follows.

BRIEF DESCRIPTION OF THE DRAWINGS

The novel features believed characteristic of the invention are set forth in the appended claims. The invention itself, however, as well as a preferred mode of use, further objectives and advantages thereof, will best be understood by reference to the following detailed description of an illustrative embodiment when read in conjunction with the accompanying drawings, wherein:

DETAILED DESCRIPTION OF THE INVENTION

Figure 1:
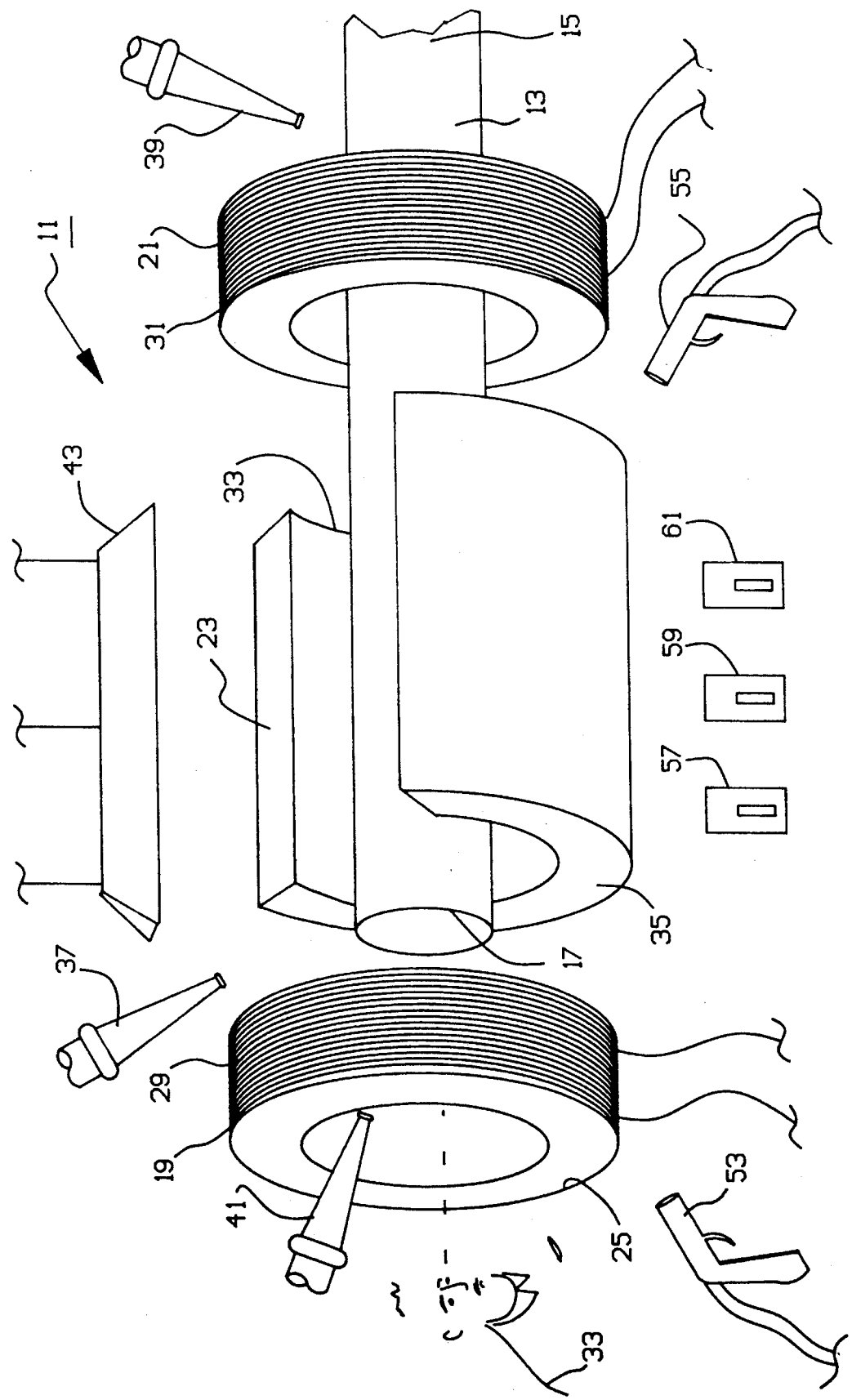
FIG. 1 is a perspective view of a variety of components which are utilized in the preferred apparatus for inspecting cylindrical or tubular ferromagnetic members for defects, in accordance with the present invention.

FIG. 1 is a perspective view of a variety of components which are utilized in the preferred apparatus for inspecting cylindrical or tubular ferromagnetic members for defects, in accordance with the present invention. The inspection apparatus 11 is composed of components which are depicted in FIGS. 1, 5, 6, 7, and 8. The components depicted in Figure I are those components which are utilized to generate longitudinal and traverse magnetic fields, to place magnetic particles on the cylindrical and tubular member, to illuminate the magnetic particles with ultraviolet light, and to marking the cylindrical and tubular member for defects. As is shown in FIG. 1, ferromagnetic tubular member 13 includes outer peripheral surface 15 and inner peripheral surface 17, each of which should be inspected to detect surface and subsurface defects which would interfere with the optimal operation of ferromagnetic tubular member 13, and in particular which would interfere with the threading of ferromagnetic tubular member 13 with either exterior or interior threads to form either a pin or box end for connecting with other tubular members.

The specific objective of this invention is to identify surface and subsurface cracks, fractures, gouges, and nicks in threaded and unthreaded wellbore tubular members. The process is particularly useful in manufacturing premium threaded tubulars. The end portions are especially important in dealing with blank stock, since they must be threaded. Any defect such as a crack or gouge in the end portions of tubular stock will result in a male or female threaded region which is defective. The threads may not hold, and may prove to be leak paths if such defects are not detected in advance. The objective of the invention is to route threaded or blank stock of wellbore tubular members through an inspection station 11 where a human visually inspects both ends of the threaded or unthreaded tubular member on the exterior and interior surfaces. Typically, the middle region of the tubular stock is inspected using a different technique, and in particular using an ultrasonic or electromagnetic inspection technique. Since the end portions are especially important, human inspectors are utilized to examine the tubular for defects.

Accordingly, it is important that the human inspectors be allowed an unobstructed view of both the outer peripheral surface 15 and the inner peripheral surface 17 of the end portions of ferromagnetic tubular member 13, when the magnetic fields are active and interacting with any magnetic particles which are deposited thereon. However, another requirement is that a longitudinal magnetic field and a traverse magnetic field be generated in a manner to allow the magnetic flux lines to pass both longitudinally and traversely through ferromagnetic tubular member 13. In prior art devices, the goal of generating traverse and longitudinal magnetic fields has been obtained at the cost of either (1) obscuring portions of the outer or inner peripheral surfaces 15, 17 of the ferromagnetic tubular member 13, or (2) rendering the interaction of the magnetic fields and magnetic particles inaccessible to human operator viewing while the magnetic fields are active. In the present invention, inspection apparatus 11 maintains good visibility of the outer peripheral surface 15 and inner peripheral surface 17 of ferromagnetic tubular member, while generating longitudinal and traverse magnetic fields in a manner which allows the human operator to view the interaction of the magnetic fields with magnetic particles, during the inspection operation.

These objectives are obtained by providing magnetic field members 19, 21 which are utilized to generate a longitudinal magnetic field which completely magnetics ferromagnetic tubular member 13, which is in good alignment with the central longitudinal axis of ferromagnetic tubular member 13, and which ensures good and even distribution of the magnetic flux lines throughout all portions of ferromagnetic tubular member 13. In the preferred embodiment of the present invention, magnetic field members 19, 21 each comprise a non-magnetic cylindrical core 25, 22 respectively, around which are disposed electrically-conductive windings 29, 31, which are oriented to be concentric to the central longitudinal axis of ferromagnetic tubular member 13, and equidistant from outer peripheral surface 15 of ferromagnetic tubular member 13. Preferably, cylindrical core 25, 27 is a cylinder which has an inner diameter of nineteen (19) inches and an outer diameter of twenty-four (24) inches, and which has a width of six and one-half (6.5) inches. Preferably, electrically-conductive windings 29, 31 comprise copper wire of 11 gauge, wound about cylindrical cores 25, 27, a number of turns in the range of 1275 to 1300 turns.

Essentially, magnetic field members 19, 21, are sufficiently large in diameter, and sufficiently small in width, to allow the inspection of inner peripheral surface 17 by a human inspector 33 who may look through the central bore of cylindrical core 25 of magnetic field member 19 to visually inspect the inner peripheral surface 17 of ferromagnetic tubular member 13. Magnetic field members 19, 21 are sufficiently large in diameter to allow the passage and inspection of ferromagnetic tubular members having diameters in the range of 2 inches and 15 inches. In the preferred embodiment of the present invention, magnetic field member 19 is separated from magnetic field member 21 by a space of approximately 28 inches. Disposed therebetween is traverse magnetic field member 23 which is preferably a ferromagnetic member which includes air gap 33 therein to allow the axial passage of ferromagnetic tubular member 13. Air gap 33 also allows a human inspector to look down upon ferromagnetic tubular member 13 and inspect the outer peripheral surface 15 while both the longitudinal and traverse magnetic fields are active and interacting with the magnetic particles which are disposed thereon. In the preferred embodiment of the present invention, traverse magnetic field member 23 is formed of high-permeability ferromagnetic material, and includes a portion which receives windings 35 of electrically-conductive wire which allows for the selective generation of a magnetic field which flows through traverse magnetic field member 23 and across air gap 33 to provide a traverse magnetic field which is substantially orthogonal to the longitudinal magnetic field generated by magnetic field members 19, 21.

Figure 2A:
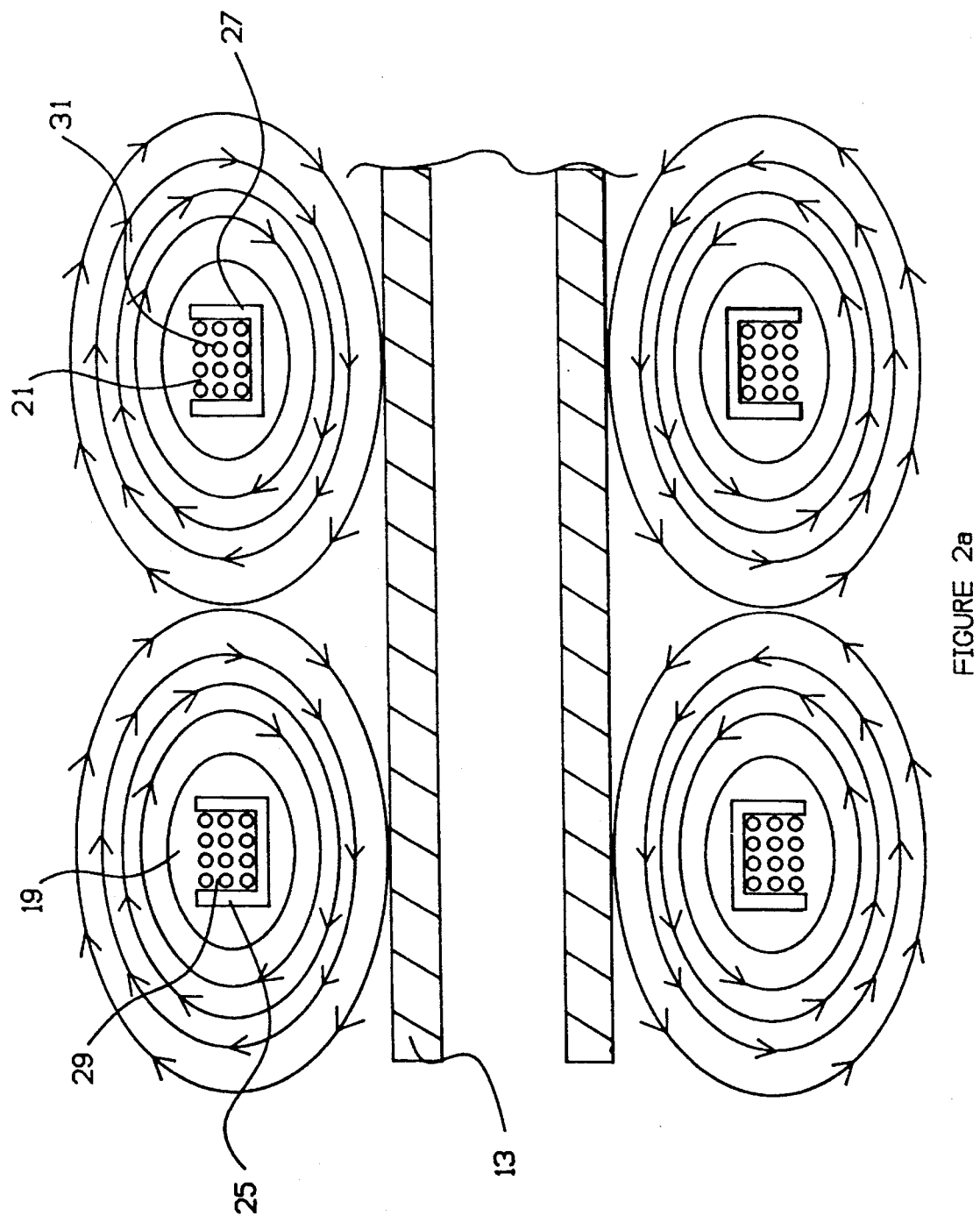
FIGS. 2a and 2b are longitudinal section views of the cylindrical member and magnetic field members which are utilized to develop a substantially longitudinal magnetic field, and in particular depict the combination of magnetic fields to generate a substantially longitudinal magnetic field.
Figure 2B:
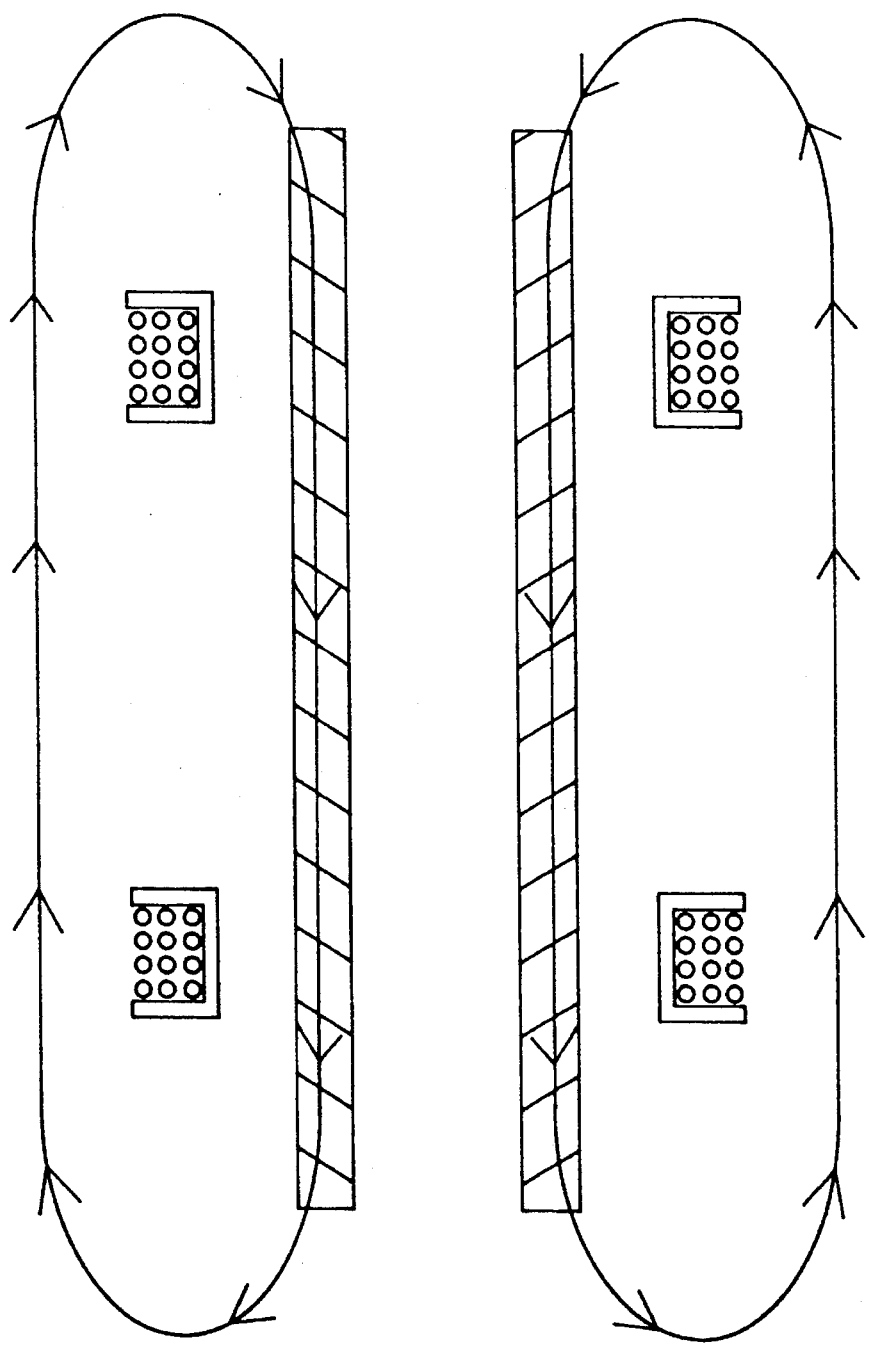
Figure 3:
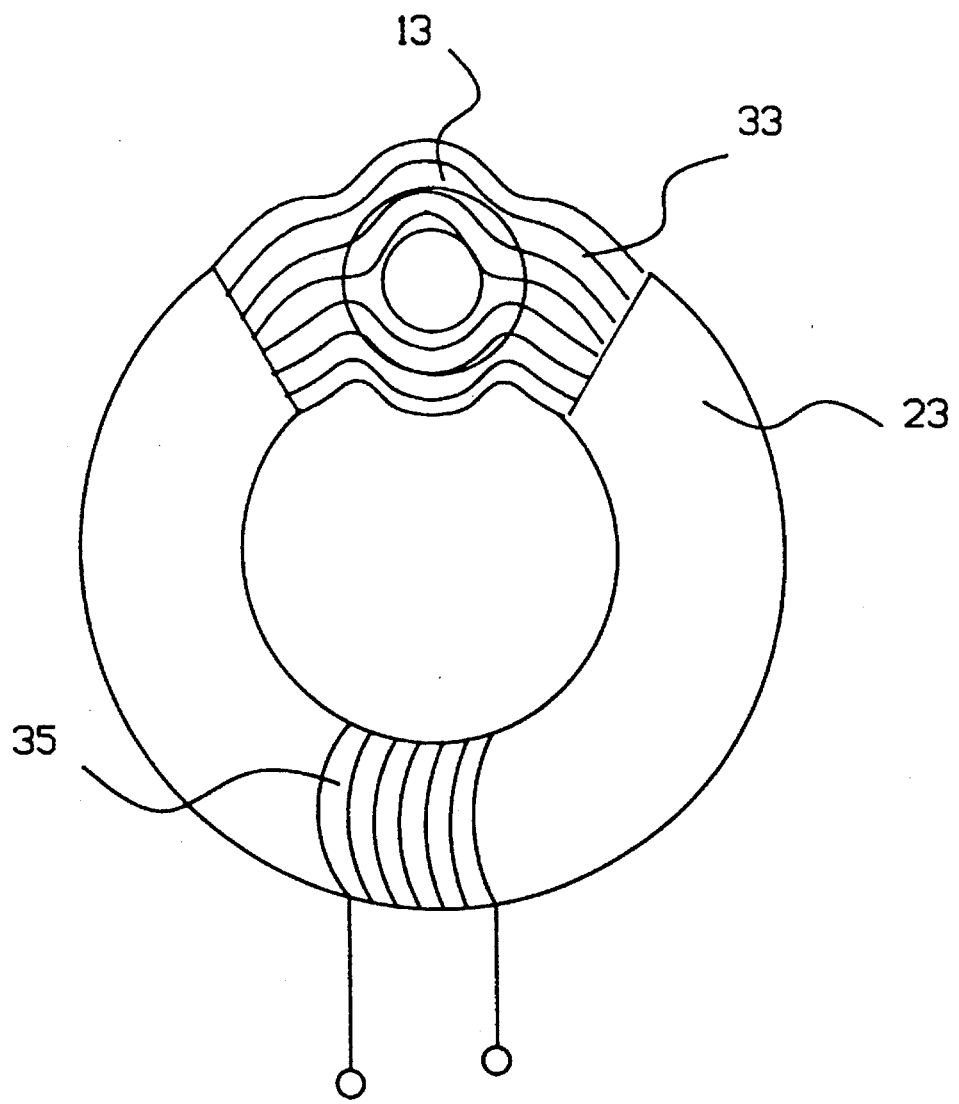
FIG. 3 is a cross-section view of a traverse magnetic field member and a tubular ferromagnetic member, which depicts the generation of a traverse magnetic field.

Turning now to FIGS. 2a, 2b and 3, the longitudinal and traverse magnetic fields which are generated by magnetic field member 19, 21 and traverse magnetic field 23 will now be described. FIGS. 2a and 2b are longitudinal section views of ferromagnetic tubular member 13. As is shown, magnetic field member 19 includes cylindrical core 25 which is concentric to ferromagnetic tubular member 13 and which carries electrically-conductive windings 29 thereon. Likewise, magnetic field member 21 includes cylindrical core 27 which is concentric to ferromagnetic tubular member 13, and which carries electrically-conductive windings 31 thereon. In the preferred embodiment of the present invention, magnetic field members 13, 19 are arranged to ensure that ferromagnetic tubular member 13 is exposed to substantially only a longitudinal magnetic field which is axially aligned therewith, and which includes flux lines which pass therethrough. Accordingly, time-varying electrical current is passed in directions through electrically-conductive windings 29, 31 which ensure the substantial cancellation of magnetic field components which do not contribute to the longitudinal magnetic field which is desired. Accordingly, time-varying current is passed through electrically-conductive windings 29, 31 into the page of FIGS. 2a, 2b at the upper portion of magnetic field member 19, 21, and which thus flows out of the page from the lower portions of magnetic field members 19, 21. This causes the generation of magnetic flux lines in the direction shown by the arrows in FIG. 2a. As is shown, the magnetic flux lines from magnetic field 19 which are orthogonal to ferromagnetic tubular member 13 are substantially cancelled by magnetic flux lines from magnetic field member 21. The resulting longitudinal magnetic field is shown in simplified form in FIG. 2b. As can be seen, the portions of the magnetic flux which do not align with the central longitudinal axis of ferromagnetic tubular member 13 are eliminated by vector addition to generate a magnetic field which (1) is evenly disposed circumferentially about ferromagnetic tubular member 13, (2) is of high field intensity at the end portions of ferromagnetic tubular member 13, and (3) is composed of substantially only longitudinal flux lines at ferromagnetic tubular member 13 to ensure the generation of only longitudinal magnetic field.

FIG. 3 is a cross-section view of traverse magnetic field member 23. As can be seen, it takes a shape which can be described as either U-shaped or C-shaped, and defines air gap 33 therein, which allows for the axial passage of ferromagnetic tubular member 13 therethrough. As is shown, windings 35 are disposed about a portion of traverse magnetic field member 23, and are utilized to generate a time-varying magnetic field which passes through ferromagnetic tubular member 13 as is shown in FIG. 3. The flux lines will pass through the material which forms ferromagnetic tubular member 13 in a generally circular configuration, and will provide a magnetic field which is substantially traverse to the longitudinal magnetic field generated by magnetic field members 19, 21. In the preferred embodiment of the present invention, traverse magnetic field member 23 is eighteen (18) inches long, and includes an air gap which is in the range of six (6) to twenty (20) inches, depending upon the diameter of the tubular member being inspected and which allows one to two inches of clearance. Windings 35 are formed from 0.144 inch by 0.040 inch square electrically conductive wire, which is wrapped about traverse magnetic field member 23 in the range of 3150 to 3200 turns.

In the preferred embodiment of the present invention, magnetic field members 19, 21 and traverse magnetic field member 23 are utilized to create longitudinal and traverse magnetic fields which are time-varying, operator-selectable, having field strengths greater than the cohesive force of the ferromagnetic member is being inspected.

Referring once again to FIG. 1, a plurality of nozzles 37, 39, 41 are provided for spraying outer peripheral surface 15 and inner peripheral surface 17 of ferromagnetic tubular member 13 with a slurry of fluorescent magnetic particles which are suspended in a water-based fluid. Nozzles 37, 39 are oriented to direct the slurry of fluorescent magnetic particles to outer peripheral surface 15 of ferromagnetic tubular member 13, while nozzle 41 is oriented to direct the slurry of fluorescent magnetic particles to inner peripheral surface 17. Ultraviolet light source 43 is suspended above inspection apparatus 11 to provide ultraviolet light which interacts with the fluorescent material to cause it to be highly noticeable to an operator performing visual inspection of outer peripheral surface 15 and inner peripheral surface 17. The interaction of the magnetic fields and the fluorescent magnetic particles is best depicted in FIGS. 4a and 4b.

Figure 4A:
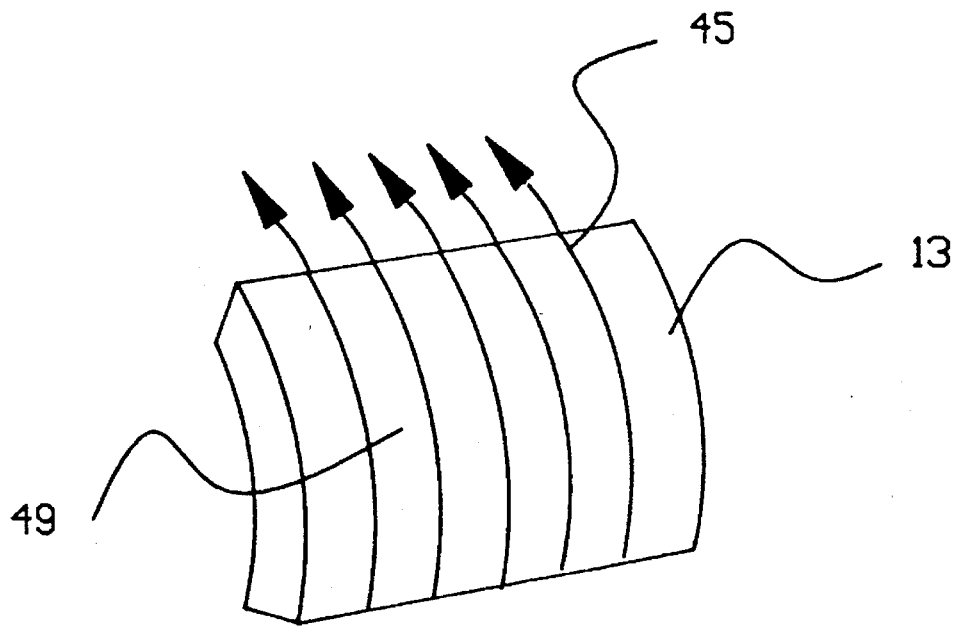
FIGS. 4a and 4b are perspective views of the utilization of longitudinal and traverse magnetic fields to detect defects in a portion of a tubular member.
Figure 4B:
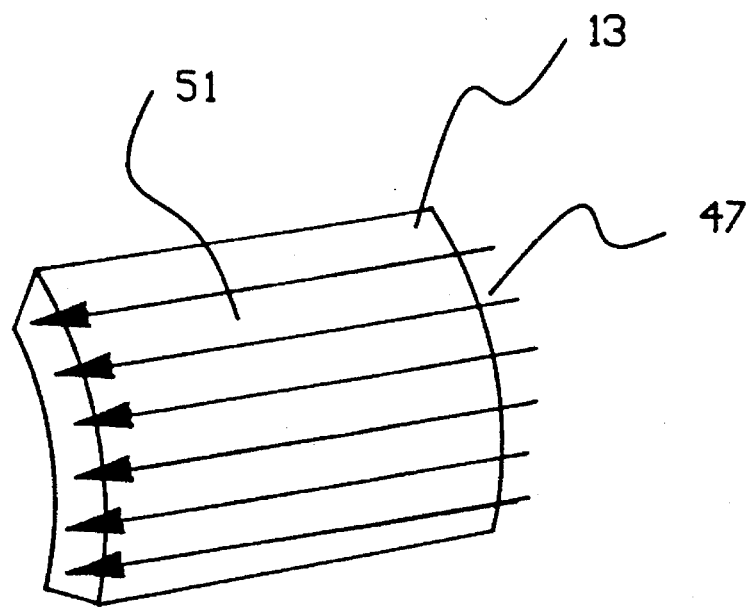

In FIG. 4a, defect 49 is shown in a portion of ferromagnetic tubular member 13. Traverse magnetic field 45 is shown in this view. Defect 49 is substantially orthogonal to traverse field 45. Defect 49 generates a stray magnetic field which attracts the fluorescent magnetic particles to cluster around and define defect 49. In FIG. 4b, defect 51 is shown in a portion of ferromagnetic tubular member 13. Longitudinal field 47 is shown also in this view. As can be seen, defect 51 is substantially orthogonal to longitudinal field 47. Defect 51 creates a stray magnetic field which attracts the fluorescent magnetic particles to cluster around and define defect 51. As is well known in the art of magnetic particle inspection, the magnetic particles provide the best and most visible definition of a defect when the magnetic field is substantially orthogonal to that defect. Since magnetic fields are vector additive, it is thus important that the longitudinal magnetic field and traverse magnetic field be applied successively to the part being inspected, or that the fields be applied to generate a cumulative magnetic field which rotates over a selected range. This can be accomplished by driving the electrically-conductive windings 29, 31 of magnetic field members 19, 21 with time-varying electrical currents which are out of phase by a preselected amount from an electrical current which drives traverse magnetic field member 23. Once a defect is detected, the human operator (or operators) may utilize paint guns 53, 55 to spray a highly visible paint (such as orange paint) upon the portion of ferromagnetic tubular member 13 which includes an unacceptable defect.

In the preferred embodiment of the present invention, ferromagnetic tubular member 13 is rotated relative to magnetic field members 19, 21 and traverse magnetic field member 23 during the inspection process, to allow the end portions of outer peripheral surface 15 and inner peripheral surface 17 to be expected. Additionally, ferromagnetic tubular member 13 must be positioned within inspection apparatus 11 for inspection, and withdrawn from inspection apparatus 11 at the termination of inspection, preferably by axial movement of ferromagnetic tubular member 13. In the preferred embodiment of the present invention, the application of fluorescent magnetic particles, the rotation of ferromagnetic tubular member 13, and the axial movement of ferromagnetic tubular member 13 may either be automatically controlled or controlled by the human operator. To allow human operator control of these operating conditions, spray control 57, rotation control 59, and axial position control 61 are provided. The automatic control of these operating parameters will be described in further detail herebelow with reference to FIGS. 6 and 7.

Figure 5:
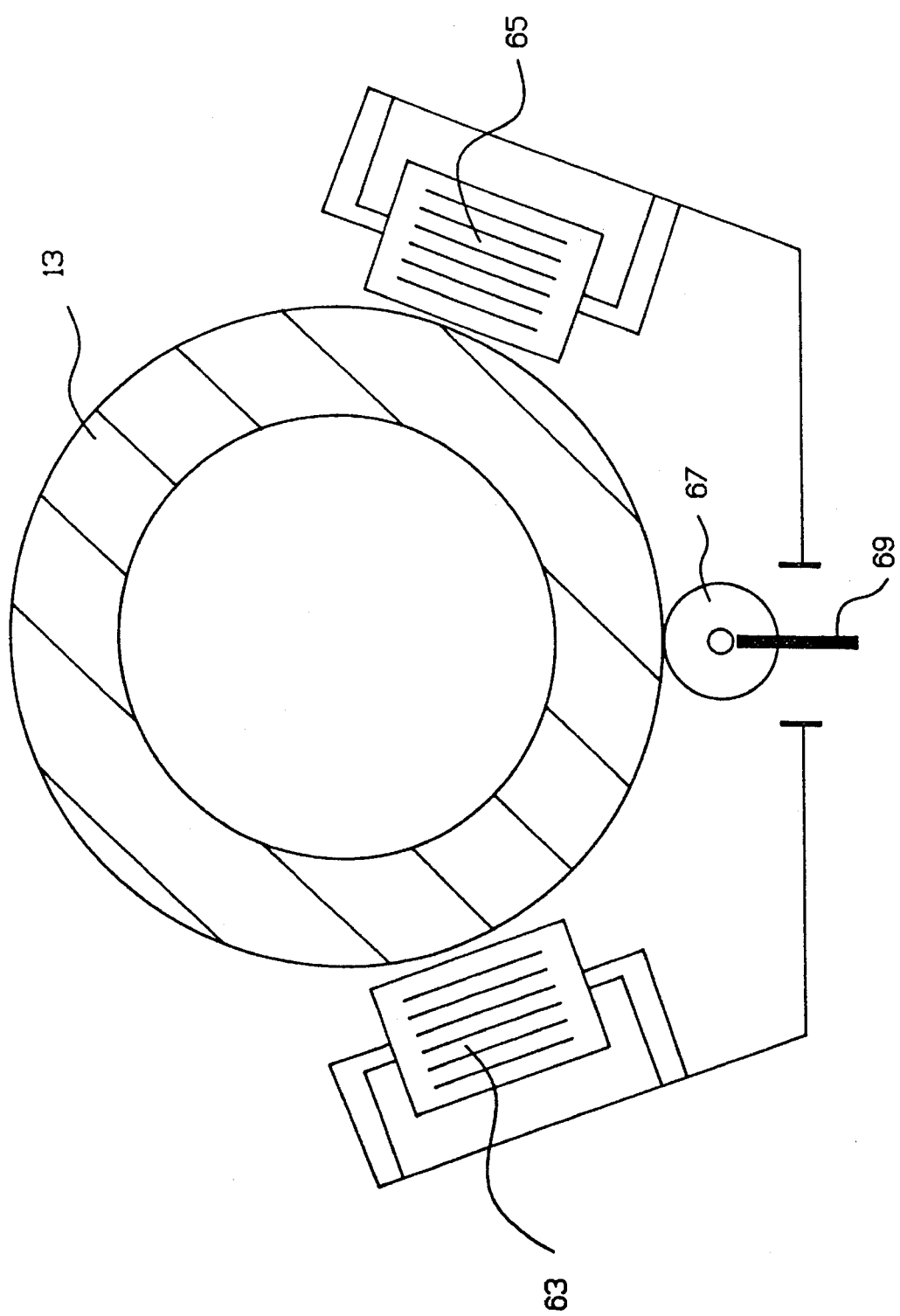
FIG. 5 is a cross-section view of a tubular member and roller devices which are utilized to longitudinally advance and retract a tubular member and rotate the tubular member.

FIG. 5 is a cross-section view of ferromagnetic tubular member 13 and the roller devices which are utilized to longitudinally advance ferromagnetic tubular member 13 and rotate ferromagnetic tubular member 13. As is shown, a plurality of axial rollers 63, 65 (the others are not depicted) are provided to control the axial position of ferromagnetic tubular member 13. Preferably, these rollers are coupled through a drive mechanism to an electric motor which is selectively energized to rotate axial rollers 63, 65 in either a clockwise or counter clockwise direction, depending upon whether the operator desires to advance or retract ferromagnetic tubular member 13 relative to inspection apparatus 11. In the preferred embodiment of the present invention, rotation roller 67 is provided for selectively engaging ferromagnetic tubular member 13, and rotating it for a preselected time interval. Also, preferably, mounting member 69 is provided to selectively raise and lower rotation roller 67 to maintain rotation roller 67 either in contact with ferromagnetic tubular member 13, or out of contact with ferromagnetic tubular member 13. Rotation roller 67 is preferably connected through a drive mechanism to an electric motor which is selectively energized to rotate rotation roller 67 in a predetermined direction.

Figure 6:
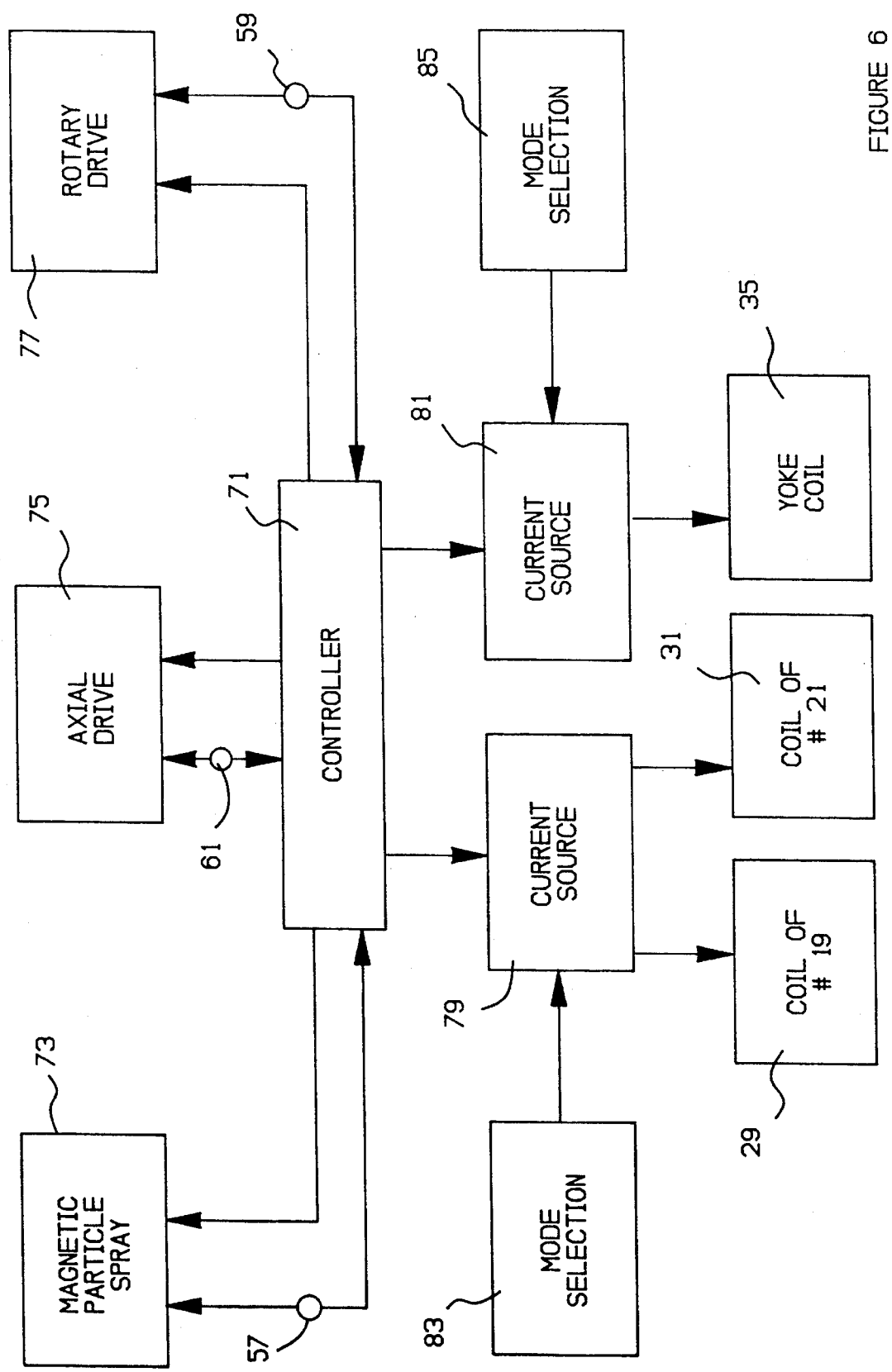
FIG. 6 is a block diagram view of the preferred embodiment of the inspection apparatus of the present invention.

FIG. 6 is a block diagram view of the preferred embodiment of the inspection apparatus of the present invention, which allows for automated control of the placement of magnetic particles on the ferromagnetic tubular member 13, the actuation of the axial drive mechanism, and the actuation of the rotary drive mechanism. As is shown, controller 71 is provided for selectively actuating magnetic particle spraying mechanism 73, axial drive mechanism 75, and rotary drive mechanism 77. Also, as is shown, the operator control mechanisms, including spray control 57, rotation control 59, and axial position control 61, allow the operator to override controller 71 and directly control the application of magnetic particles, the actuation of the axial drive mechanism 75, and the actuation of rotary drive mechanism 77. In the preferred embodiment of the present invention, controller 71 comprises a programmable logic controller (PLC) manufactured by Allen-Bradley, which is identified by Model No. PLC-2116. Also, as is shown in FIG. 6, controller 71 is utilized to control the operation of current source 79 and current source 81. As will be described in detail herebelow, current source 79 is utilized to energize the electrically-conductive windings 29, 31 of magnetic field members 19, 21. Current source 81 is utilized to selectively energize windings 35 of traverse magnetic field member 23. As was discussed above, the time-varying current provided by current sources 79, 81 should be out of phase by a selected, and preferably user-controlled, amount to ensure that the longitudinal magnetic field and the traverse magnetic field are either (1) traverse to one another, or (2) successively applied to ferromagnetic tubular member 13, to maximize the detection of defects contained in ferromagnetic tubular member 13. Mode selection mechanisms 83, 85 are provided to control the type of time-varying current applied to the various coils, and allow the operator to control the amount of phase between the time-varying currents which are utilized to generate the time-varying longitudinal and traverse magnetic fields.

Figure 8:
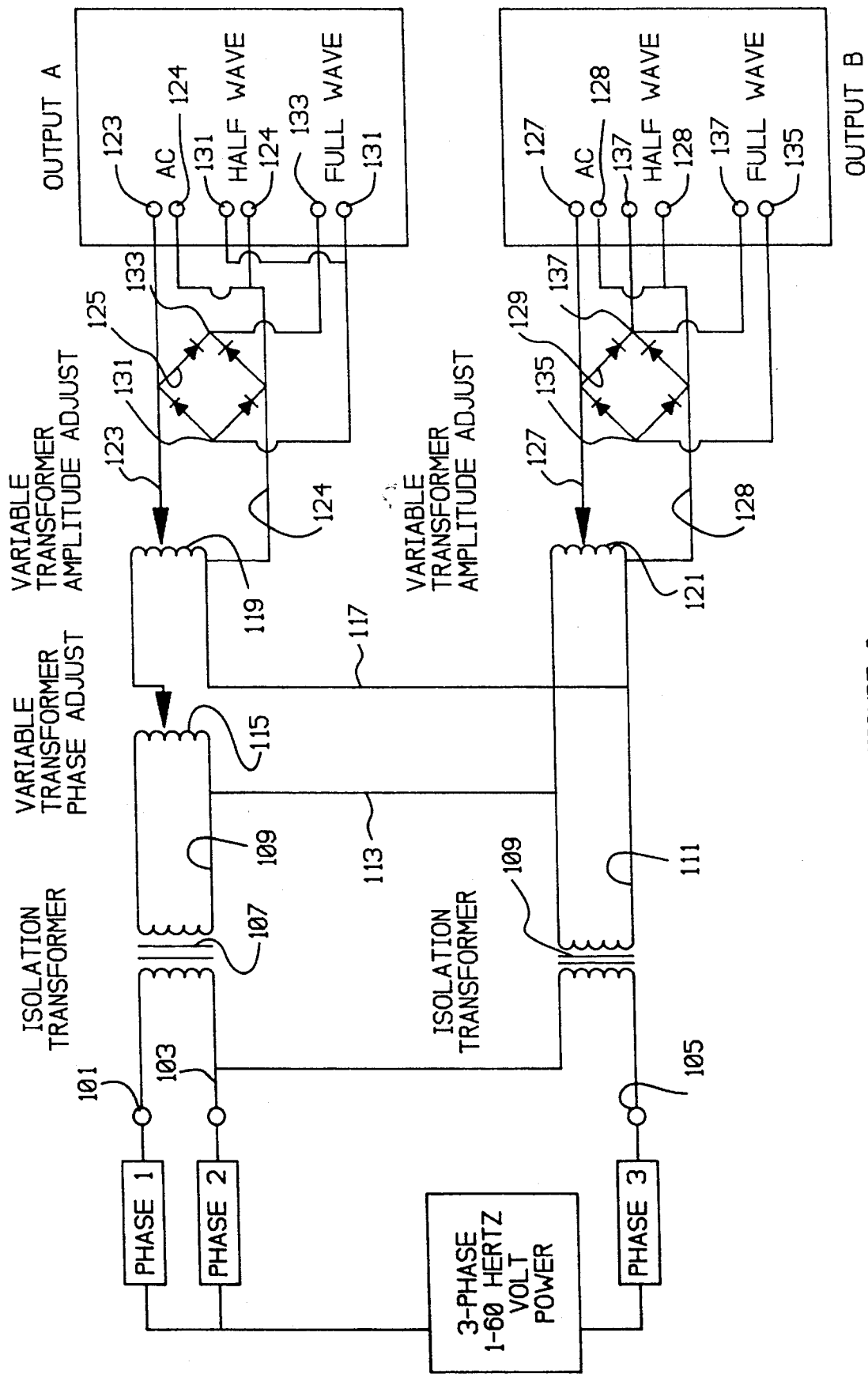
FIG. 8 is a electrical circuit schematic view of a circuit which is utilized to develop driving current for the longitudinal and traverse magnetic fields.
Figure 9A:
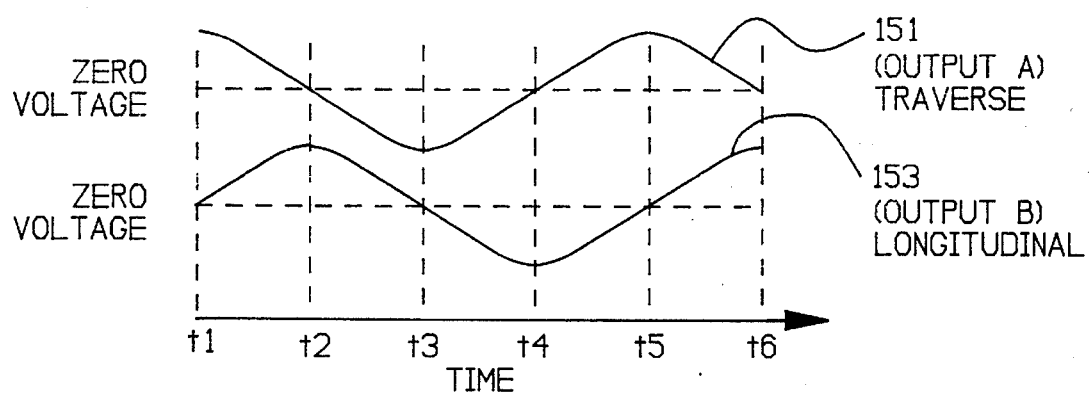
FIGS. 9a, 9b and 9c are graphic depictions of the types of current which can be generated with the circuit of FIG. 8.
Figure 9B:
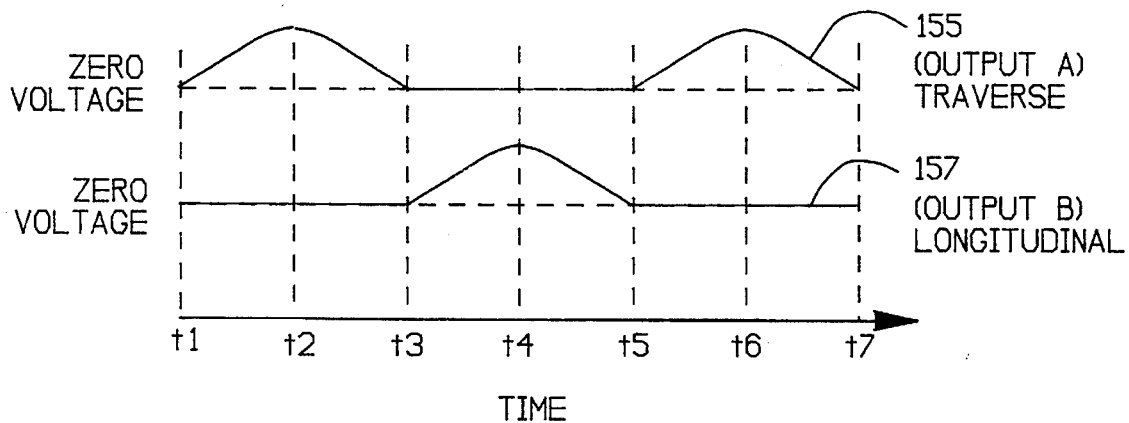
Figure 9C:
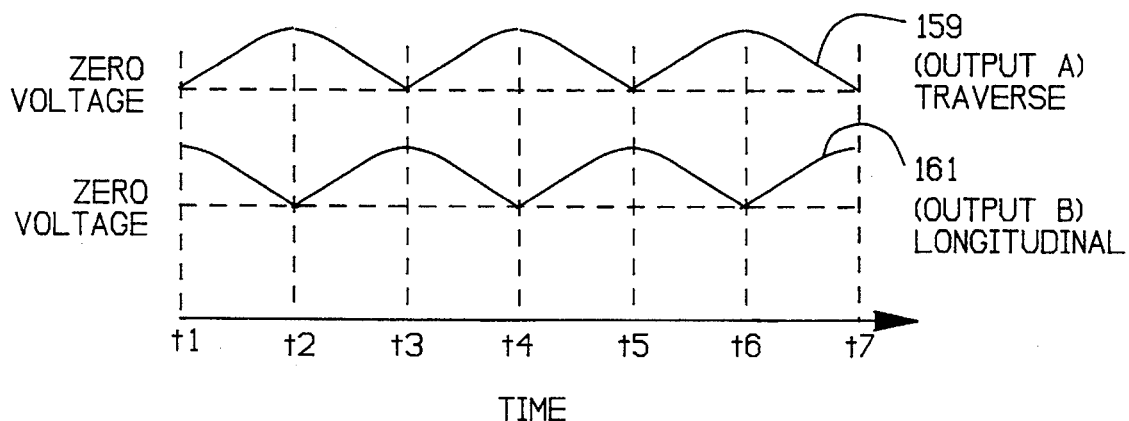

FIG. 8 is an electrical schematic depiction of an electrical circuit which is utilized to develop the time-varying driving currents for the coils which generate the time-varying longitudinal and traverse magnetic fields. FIGS. 9a, 9b, and 9c provide graphic depictions of types of fields which can be generated with the electrical circuit depicted in FIG. 8.

With reference now to FIG. 8, three-phase power is provided at an input to this electrical circuit. The output of this circuit is time-varying current which can be either (1) an ordinary alternating current waveform, (2) a half-wave rectified alternating current waveform, or (3) a full-wave rectified alternating current waveform. In the preferred embodiment of the present invention, the operator, or the controller 71 acting upon program instructions from the operator, may select the phase difference between (a) the time-varying current supplied to the electrically-conductive windings 29, 31 of magnetic field members 19, 21 and (b) the time-varying current supplied to windings 35 of traverse magnetic field member 23. Additionally, the amplitude of the time-varying current may be controlled by the operator. As is shown in FIG. 8, phase one of the three-phase power is supplied to input terminal 101, phase two of the three-phase power is supplied to input terminal 103, and phase three of the three-phase power is supplied to input terminal 105. The voltage difference between input terminals 101 and 103 is passed across isolation transformer 107 to phase adjust circuit 109. The voltage difference between input terminals 103 and 105 is passed across isolation transformer 109 to amplitude adjust circuit 111. Conductor 113 links phase adjust circuit 109 and amplitude adjust circuit 111, as is shown. In phase adjust circuit 107, variable transformer 115 is utilized to adjust the phase difference between output A and output B to a user-selected amount of phase difference in the range of ninety degrees of phase difference to one hundred and eighty degrees of phase difference. Variable transformer 119 is utilized to allow the operator to select the amplitude of output A. Variable transformer 121 is utilized to allow the operator to select the amplitude of output B. Variable transformers 119 and 121 are connected through conductor 117.

The output of variable transformer 119 is applied to the input nodes of diode bridge 125. Likewise, the output of variable transformer 121 is applied to the input nodes of diode bridge 129. The voltage between nodes 123, 124 (the output of variable inductor 119) is the un-rectified alternating current having operator-selected amplitude and phase. This output is represented by the letters "AC" in output A. The half-wave rectified alternating current output (which is designated by "HALF-WAVE" in output A) is the current provided between node 131 of diode bridge 125 and node 124. The full-wave rectified alternating current output (identified in output A as "FULL-WAVE") is the current between node 133 and node 131 of diode bridge 125.

With reference now to output B, the un-rectified alternating current output between nodes 127, 128 is identified in output B as "AC". The half-wave rectified current is the current between node 137 of diode bridge 129 and node 128. The full-wave rectified alternating current output is the current between node 137 of diode bridge 129 and node 135 of diode bridge 129.

In the preferred embodiment of the present invention, a selected alternating current from output A is coupled to electrically-conductive winding 35 of traverse magnetic field member 23, while a corresponding alternating current waveform from output B is applied to electrically-conductive windings 29, 31 of magnetic field members 19, 21. Variable transformer 115 is utilized to adjust the phase difference between output A and output B in the range of ninety degrees to one hundred and eighty degrees of phase difference. Variable inductor 119, 112 are utilized to control the amplitude of the signal provided by output A and output B.

FIGS. 9a, 9b, and 9c graphically depict the types of time-varying magnetic fields which may be supplied by electrically conductive windings 29, 31 of magnetic field members 19, 21, and windings 35 of traverse magnetic field member 23. FIG. 9a graphically depicts traverse field 151 and longitudinal field 153, while the electrically conductive windings 29, 31 are driven by an alternating current which is ninety degrees out of phase with the alternating current which drives windings 35. Note that when traverse magnetic field 151 is at a positive maximum intensity, longitudinal field 153 is at zero intensity. Likewise, note that when traverse field 151 is at a negative maximum intensity, longitudinal field 153 is at a zero intensity. In essence, the cumulative magnetic field rotates as a function of time at the region being inspected in ferromagnetic tubular member 13.

FIG. 9b is a graphic depiction of traverse field 155 and longitudinal field 157 when driven by a half-wave rectified alternating current which is 180 degrees out of phase, with output A driving windings 35 of traverse magnetic field member 23, and with output B driving electrically-conductive windings 29, 31 of magnetic field members 19, 21. Note that the traverse and longitudinal magnetic fields are successively applied to ferromagnetic tubular member 13. As is shown in FIG. 9b, during the period of $t_1$ to $t_3$, the traverse field alone is applied to ferromagnetic tubular member 13. During the time period of $t_3$ to $t_5$, the longitudinal magnetic field alone is applied to ferromagnetic tubular member 13. Thus, the traverse and longitudinal magnetic fields are successively applied to the tubular member being expected.

FIG. 9c is a graphic depiction of traverse magnetic field 159 and longitudinal magnetic field 161, with windings 35 of traverse magnetic field member 23 being driven by full-wave rectified alternating current from output B, and with electrically-conductive windings 29, 31 of magnetic field members 19, 21 being driven by full-wave rectified alternating current from output B. As is shown, when the traverse magnetic field 159 is at a maximum amplitude, the longitudinal magnetic field 161 is at a minimum amplitude. Additionally, when the amplitude of the longitudinal field 161 is at a maximum amplitude, the amplitude of traverse magnetic field 159 is at a minimum amplitude. In this mode the cumulative magnetic field rotates in position relative to ferromagnetic tubular member 13.

In summary, the particular windings of magnetic field member 19, magnetic field member 21, and traverse magnetic field member 23 may be driven by time-varying electrical currents which have user-selectable (1) amplitudes, (2) degrees of rectification, and (3) phase differences between coils driven by output A and output B. This allows for the application of longitudinal and traverse magnetic fields which vary in orientation over a predetermined range (such as the examples of FIGS. 9a and 9c), but which can be successively applied also (such as the example of FIG. 9b), if desired.

As was discussed above, controller 71 of FIG. 6 may be utilized to automatically perform some of the operations which are necessary for the inspection of ferromagnetic tubular member 13 in accordance with the present invention. Principally, controller 71 may be utilized to automatically (1) spray magnetic particles on ferromagnetic tubular member 13, (2) operate the axial drive 75 to advance and retract the ferromagnetic tubular member 13, (3) actuate rotary drive 77 to rotate ferromagnetic tubular member 13 for a predetermined time interval, (4) apply current from current source 79 in accordance with operator selection of the current waveform through utilization of mode selection 83, and (5) apply current from current source 81 in accordance with the operator selection regarding the alternating current waveform as determined by mode selection 85. In the preferred embodiment of the present invention, the mode selection apparatus 85, comprises electrical switches which selectively couple output A and output B of the electrical circuit of FIG. 8 to electrically-conductive windings 29, 31 of magnetic field members 19, 21 and windings 35 of traverse magnetic field member 23. Controller 71 may be programmed with instructions which automate the operation of magnetic particle spray apparatus 73, axial drive 75 and rotary drive 77, and which operates conventional switches to selectively connect current sources 79, 81 to the plurality of coils which provide the longitudinal and traverse magnetic fields.

Figure 7:
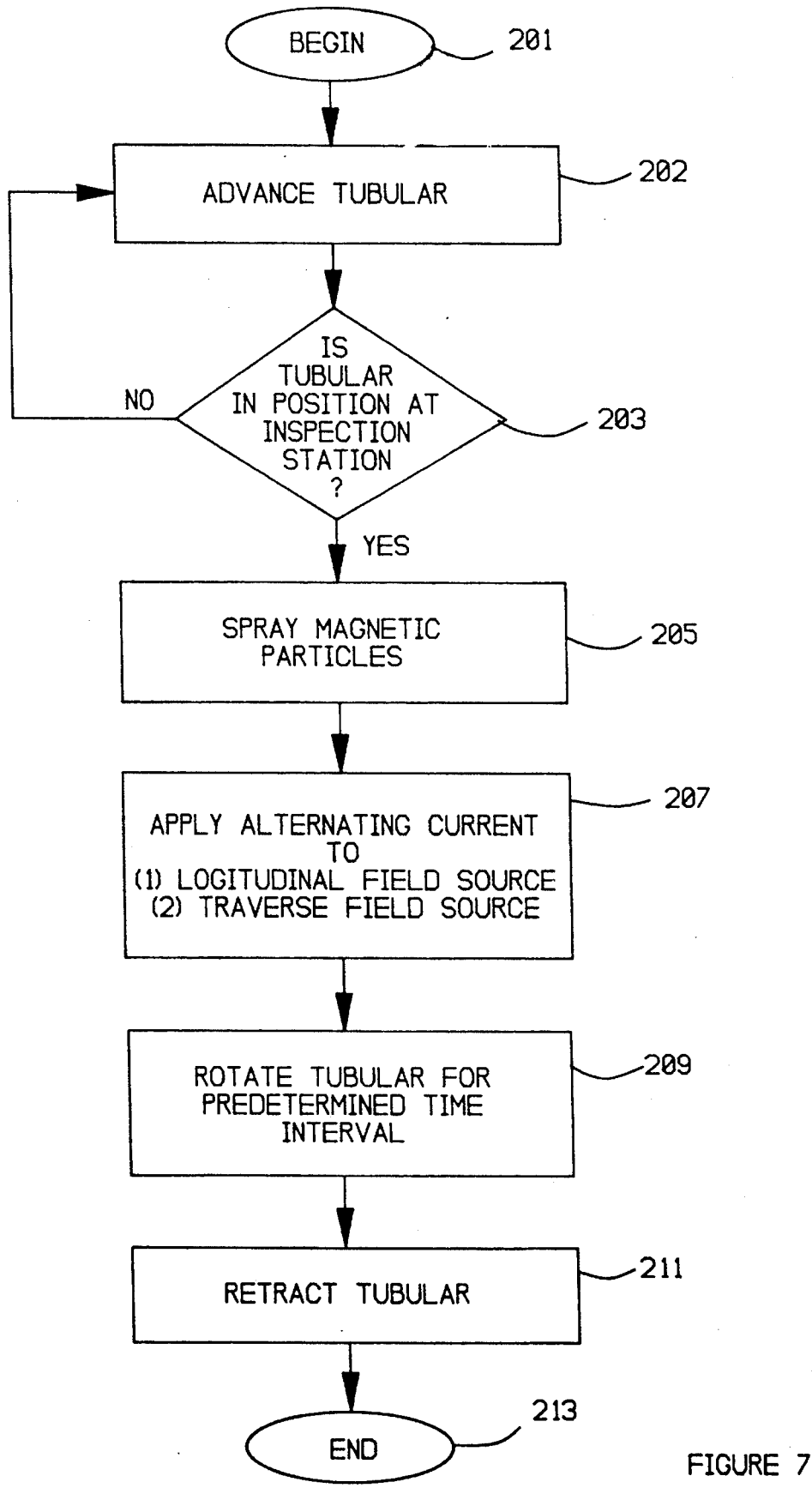
FIG. 7 is a flowchart representation of a computer program which is executed by the controller of FIG. 6 to automatically perform functions of the inspection apparatus.

One type of program for controller 71 is set forth in flowchart form in FIG. 7. The process begins at step 201, and continues at step 202, wherein controller 71 operates axial drive 75 to advance ferromagnetic tubular member 13 a preselected distance, to place it in a location within inspection apparatus 11 which allows magnetic particle inspection operations to be performed upon it. In step 203, controller 71 determines whether the ferromagnetic tubular member 13 is in position at inspection station 11. The position of ferromagnetic tubular member 13 can be determined through utilization of a photoelectric eye, which is conventional for determining the placement of tubular members. If the tubular is not in position, the process continues at step 202, wherein the ferromagnetic tubular member 13 is advanced. If it is determined, however, in step 203, that the ferromagnetic tubular member 13 is in the correct position, the process continues at step 205, wherein controller 71 applies power to an electrically-actuated pumping device which pumps fluorescent magnetic particles from a reservoir and through fluid nozzles 37, 39, 41, causing the spraying deposition of the fluorescent magnetic particles on the outer and inner peripheral surfaces 15, 17 of the end portion of ferromagnetic tubular member 13.

The operation continues at step 207, wherein controller 71 actuates electrical switches which connects current sources 79, 81 to the windings 29, 31, 35 of magnetic field members 19, 21 and traverse magnetic field member 23 to generate the longitudinal and traverse magnetic fields in accordance with the operator settings as determined by mode selection blocks 83, 85. Concurrently with the application of the longitudinal and traverse magnetic fields, controller 71 actuates rotary drive 77, causing ferromagnetic tubular member 13 to be rotated for a predetermined time interval. In the preferred embodiment of the present invention, the time interval should be sufficiently long to allow three to four complete revolutions of ferromagnetic tubular member 13, to allow full and accurate human inspection of outer and inner peripheral surfaces 15, 17 of ferromagnetic tubular member 13. Then, in accordance with step 211, ferromagnetic tubular member 13 is retracted from inspection apparatus 11 by controller 71 actuation of axial drive 75. Finally, the process ends at step 213.

Figure 10:
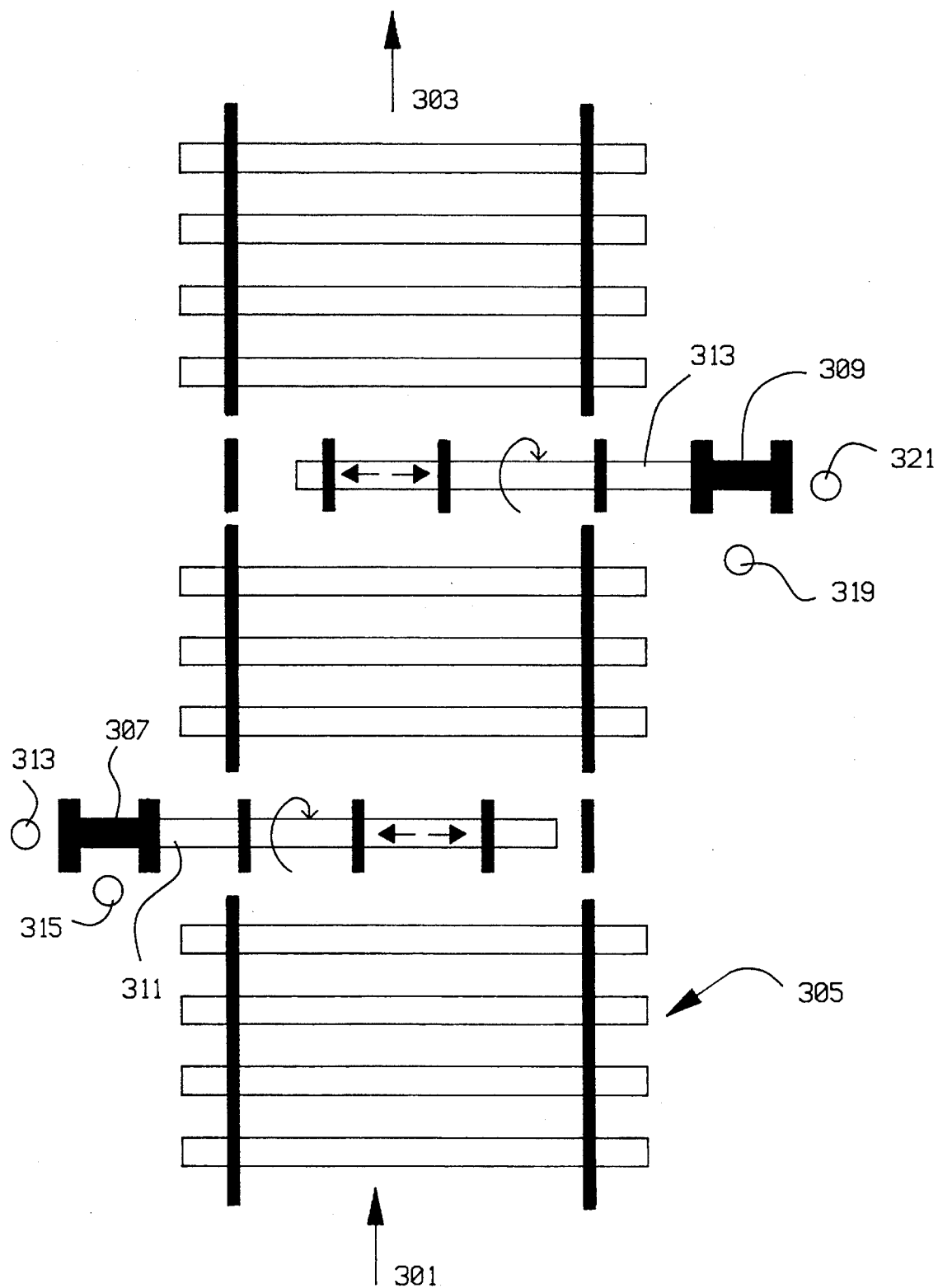
FIG. 10 is a schematic representation of an assembly line inspection apparatus.

As a practical matter, it is necessary to inspect both ends of ferromagnetic tubular member 13, but such inspection should be conducted in a manner which ensures the safety of the human inspectors. FIG. 10 provides a top plan view of a mass-production inspection technique, wherein both ends of ferromagnetic tubular member may be inspected, while ensuring the safety of the human inspectors. As is shown in FIG. 10, pipes 305 are advanced from the direction of arrow 301 toward the direction of arrow 303. Inspection station 307 is provided to the left of the advancing pipes, while inspection station 309 is provided to the right of the advancing pipes. Each of inspection stations 307, 309 include all the components which have been discussed herein to allow full inspection of the end of the pipes' outer and inner peripheral surfaces. Therefore, inspection station 307 includes a plurality of magnetic field members which generate a longitudinal magnetic field, without obstructing the operator's view of the outer and inner peripheral surfaces, as well as a traverse magnetic field member which also allows substantially unimpeded viewing of the outer peripheral surface of the pipe. Inspection station 309 is similarly equipped. When pipe 311 reaches a location which is adjacent inspection station 307, it is axially advanced outward from the rack mechanism, and is placed in position for rotation and inspection, preferably by human inspectors 313, 315. Inspector 313 views the inner peripheral end portion of pipe 311, while inspector 315 views the outer peripheral surface of pipe 311. Inspector 315 may override the automatic operation of inspection station 307 to directly control the application of fluorescent particles, the axial position of pipe 311, and the rotation of pipe 311. All this is done without endangering either inspectors 313 or 315. The same is true for inspection station 309. When pipe 313 is located in the position adjacent inspection station 309, it is axially advanced toward inspection station 309 until it is in a position to receive magnetic particles, and be rotated. Human inspectors 319, 321 view the end portion of pipe 313 during the inspection process. Inspector 319 views the outer peripheral portion of the end of pipe 313, while inspector 321 views the inner peripheral portion of pipe 313.

The present invention allows for the substantially unobstructed human inspection of the ends of tubular members while the traverse and longitudinal magnetic fields are being applied thereto, and interacting with the fluorescent magnetic particles deposited thereon. This provides significant advances over prior art devices, and allows for a more accurate and efficient inspection of cylindrical and tubular members than has heretofore been possible.

While the invention has been shown in only one of its forms, it is not thus limited but is susceptible to various changes and modifications without departing from the spirit thereof.

What is claimed is:

1. A method of inspecting a cylindrical ferromagnetic member for defects, comprising the method steps of:

providing a plurality of magnetic field members, each selectively generating a time-varying magnetic field, for combination into a time-varying composite longitudinal magnetic field with magnetic flux lines which are substantially aligned with a central longitudinal axis of said cylindrical ferromagnetic member;

providing a traverse magnetic field member which selectively generates a time-varying traverse magnetic field with magnetic flux lines which are substantially traverse to said central longitudinal axis of said cylindrical ferromagnetic member;

arranging (a) said plurality of magnetic field members and (b) said traverse magnetic field member to provide an unobstructed view of:
  (a) an outer peripheral portion of said cylindrical ferromagnetic member; and
  (b) an inner peripheral portion of any central bore extending through said cylindrical ferromagnetic member;

placing a slurry containing ferromagnetic particles on selected portions of said cylindrical ferromagnetic member, including:
  (a) said outer peripheral portion of said cylindrical ferromagnetic member; and
  (b) said inner peripheral portion of any central bore extending through said cylindrical ferromagnetic member maintaining (a) said plurality of magnetic field members and (b) said traverse magnetic field member out of contact with said cylindrical ferromagnetic member;

applying (a) said time-varying composite longitudinal magnetic field and (b) said time-varying traverse magnetic field to said cylindrical ferromagnetic member;

wherein said plurality of magnetic field member comprise a plurality of current-carrying windings (a) each concentric to said central longitudinal axis of said cylindrical ferromagnetic member and (b) spaced apart along said central longitudinal axis; and wherein, during said step of applying, time-varying current is passed through said plurality of current-carrying windings, in directions which ensure cancellation of magnetic field components adjacent said cylindrical ferromagnetic member which do not contribute to said time-varying composite longitudinal magnetic field;

rotating said cylindrical ferromagnetic member;

detecting said defects in said cylindrical ferromagnetic member from accumulations of said magnetic particles at leakage fields corresponding to magnetic discontinuities of defects in said cylindrical ferromagnetic member.

2. A method according to claim 1, wherein said plurality of magnetic field members comprise:

a plurality of current-carrying windings (a) each generally concentric to said central longitudinal axis of said cylindrical ferromagnetic member and (b) spaced apart along said central longitudinal axis.

3. A method according to claim 1, wherein said traverse magnetic field member comprises:

a ferromagnetic magnetic flux pathway with an air-gap defined therein for axial passage of said cylindrical ferromagnetic member.

4. A method according to claim 1, wherein said step of applying comprises:

applying (a) said time-varying composite longitudinal magnetic field and (b) said time-varying traverse magnetic field to said cylindrical ferromagnetic member, with a phase difference therebetween.

5. A method according to claim 4, further comprising:

selecting a phase difference for said time-varying composite longitudinal magnetic field and said time-varying traverse magnetic field.

6. A method according to claim 1, wherein said step of placing comprises:

placing a slurry containing ferromagnetic particles on selected portions of said cylindrical ferromagnetic member.

7. A method according to claim 1, further comprising:

providing a controller for executing a program resident in memory;

utilizing said program to automatically perform at least one of the following steps:
 (a) said step of placing magnetic particles on selected portions of said cylindrical ferromagnetic member;
 (b) said step of applying said time-varying composite longitudinal magnetic field and said time-varying traverse magnetic field to said cylindrical ferromagnetic member; and
 (c) said step of rotating said cylindrical ferromagnetic member.

8. A method of inspecting a plurality of cylindrical ferromagnetic members for defects, comprising the method steps of:

(i) providing at least one inspection station with:
 (a) a plurality of magnetic field members, each selectively generating a time-varying magnetic field, for generating a time-varying longitudinal magnetic field with magnetic flux lines which are substantially aligned with a central longitudinal axis of each of said plurality of cylindrical ferromagnetic members; and
 (b) a traverse magnetic field member which selectively generates a time-varying traverse magnetic field with magnetic flux lines which are substantially traverse to said central longitudinal axis of each of said plurality of cylindrical ferromagnetic members;

(ii) arranging said plurality of magnetic field members and said traverse magnetic field member to provide an unobstructed view of:
 (a) an outer peripheral portion of each of said plurality of cylindrical ferromagnetic members; and
 (b) an inner peripheral portion of any central bore extending through each of said plurality of cylindrical ferromagnetic members;
while each of said plurality of cylindrical ferromagnetic members is disposed in said at least one inspection station;

(iii) providing a controller for executing a program resident in memory;

(iv) utilizing said program to automatically successively perform at least one of the following steps:
 (a) advancing said plurality of cylindrical ferromagnetic members through said at least one inspection station;
 (b) placing magnetic particles on selected portions of each of said plurality of cylindrical ferromagnetic members;
 (c) applying said time-varying longitudinal magnetic field and said time-varying traverse magnetic field to each of said plurality of cylindrical ferromagnetic members; and
 (d) rotating each of said plurality of cylindrical ferromagnetic members;
while maintaining said plurality of magnetic field members and said traverse magnetic field member out of contact with each of said plurality of cylindrical ferromagnetic members;

wherein said plurality of magnetic field members comprise a plurality of current-carrying windings (a) each generally concentric to said longitudinal axis of said plurality of cylindrical ferromagnetic members, and (b) spaced apart a selected distance from one another; and wherein said step of applying includes driving said plurality of current-carrying windings with time-varying current in directions which ensure cancellation of magnetic field components adjacent said plurality of cylindrical ferromagnetic members which do not contribute to said time-varying longitudinal magnetic field;

(v) detecting said defects in each of said plurality of cylindrical ferromagnetic members from accumulations of said magnetic particles at leakage fields corresponding to magnetic discontinuities of defects in said plurality of cylindrical ferromagnetic members.

9. A method according to claim 8, wherein said step of placing magnetic particles comprises:

placing a slurry including magnetic particles on selected portions of each plurality of cylindrical ferromagnetic members.

10. A method according to claim 8:

wherein each of said plurality of magnetic field members includes an axial pathway therethrough; and wherein said step of advancing comprises sequentially advancing said plurality of cylindrical ferromagnetic members through said plurality of magnetic field members of said at least one inspection station by passing said plurality of cylindrical ferromagnetic members through said axial pathway of each of said plurality of magnetic field members.

11. A method according to claim 8:

wherein said traverse magnetic field member comprises a ferromagnetic magnetic flux pathway with an air-gap defined therein; and wherein said step of advancing comprises sequentially advancing said plurality of cylindrical ferromagnetic members through said air-gap of said ferromagnetic magnetic flux pathway.

12. A method according to claim 8, wherein said plurality of cylindrical ferromagnetic members includes first and second ends, further comprising:

providing one inspection station for said first end of each of said plurality of cylindrical ferromagnetic members and another inspection station for said second end of said plurality of cylindrical ferromagnetic members; and successively detecting defects in said first end and said second end of each of said plurality of cylindrical ferromagnetic members.

13. An apparatus for inspecting a cylindrical ferromagnetic member for defects, comprising:

a plurality of magnetic field members, each selectively generating a time-varying magnetic field, for combination into a time-varying composite longitudinal magnetic field with magnetic flux lines which are substantially aligned with a central longitudinal axis of said cylindrical ferromagnetic member;

wherein said plurality of magnetic field member comprise a plurality of current-carrying windings (a) each concentric to said central longitudinal axis of said cylindrical ferromagnetic member and (b) spaced apart along said central longitudinal axis; and wherein time-varying current is passed through said plurality of current-carrying windings, in directions which ensure cancellation of magnetic field components adjacent said cylindrical ferromagnetic member which do not contribute to said time-varying composite longitudinal magnetic field;

a traverse magnetic field member which selectively generates a time-varying traverse magnetic field with magnetic flux lines which are substantially traverse to said central longitudinal axis of said cylindrical ferromagnetic member;

means for placing magnetic particles on selected portions of said cylindrical ferromagnetic member, including:
(a) said outer peripheral portion of said cylindrical ferromagnetic member; and
(b) said inner peripheral portion of any central bore extending through said cylindrical ferromagnetic member;

means for selectively applying (a) said time-varying composite longitudinal magnetic field and (b) said time-varying traverse magnetic field to said cylindrical ferromagnetic member;

means for rotating said cylindrical ferromagnetic member;

a viewing region for allowing unobstructed operator detection of defects in said cylindrical ferromagnetic member from accumulations of said magnetic particles at leakage fields corresponding to magnetic discontinuities of defects in said cylindrical ferromagnetic member wherein said viewing region allows unobstructed operator inspection of:
(a) an outer peripheral portion of said cylindrical ferromagnetic member; and
(b) an inner peripheral portion of any central bore extending through said cylindrical ferromagnetic member.

14. An apparatus according to claim 13, wherein said plurality of magnetic field members include a plurality of current-carrying windings (a) each generally concentric to said central longitudinal axis of said cylindrical ferromagnetic member and (b) spaced apart along said central longitudinal axis.

15. An apparatus according to claim 13, wherein said traverse magnetic field member comprises a ferromagnetic magnetic flux pathway with an air-gap defined therein for axial passage of said cylindrical ferromagnetic member.

16. An apparatus according to claim 13, further comprising:

a controller for executing a program resident in memory to automatically perform at least one of the following operations:
(a) placing magnetic particles on selected portions of said cylindrical ferromagnetic member;
(b) applying said time-varying composite longitudinal magnetic field and said time-varying traverse magnetic field to said cylindrical ferromagnetic member; and
(c) rotating said cylindrical ferromagnetic member.

* * * * *